United States Patent [19]

Laforest et al.

[11] 4,042,620
[45] Aug. 16, 1977

[54] CONTINUOUS PROCESS FOR THE PRODUCTION OF MAEAMIC ACIDS

[75] Inventors: Jean Laforest, St. Cyr au Mont d'Or; Louis Silhol, St. Genis Laval; Pierre Renard, Villeurbanne, all of France

[73] Assignee: Rhone-Poulenc, S.A., Paris, France

[21] Appl. No.: 571,108

[22] Filed: Apr. 24, 1975

Related U.S. Application Data

[63] Continuation of Ser. No. 432,646, Jan. 11, 1974, abandoned.

[30] Foreign Application Priority Data

Jan. 16, 1973   France .................................. 73.01405

[51] Int. Cl.² ............................................. C07C 51/00
[52] U.S. Cl. ........................... 260/518 R; 260/389; 260/514 K; 260/308 R; 260/534 R
[58] Field of Search ..................... 260/534 R, 518 R

[56] References Cited

U.S. PATENT DOCUMENTS

| 2,459,964 | 1/1949 | Robinson et al. | 260/534 |
|---|---|---|---|
| 2,723,991 | 11/1955 | Sears et al. | 260/518 |
| 2,793,231 | 5/1957 | Newby et al. | 260/534 |
| 3,947,493 | 3/1976 | Balma et al. | 260/518 R |

Primary Examiner—James O. Thomas, Jr.
Assistant Examiner—James H. Reamer
Attorney, Agent, or Firm—Stevens, Davis, Miller & Mosher

[57] ABSTRACT

A continuous process is provided for the preparation of a maleamic acid of the formula:

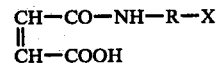

in which: R represents a linear or branched alkylene, arylene, aralkylene, alkylarylene or cycloalkylene radical or a divalent heterocyclic radical, the free valencies of which are attached to carbon atoms, the radical containing 2 to 20 carbon atoms and X represents either a hydrogen atom or the radical:

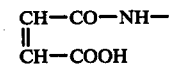

which comprises passing a solution of a primary monoamine or diamine and a solution of maleic anhydride in amounts such that there is a 5 to 20 mol % excess of anhydride, at a temperature of from 40° to 130° C and at a rate greater than 7 m/second through an injection nozzle into a twin screw reactor, the solvent for the primary amine being the same as, or compatible with, the solvent for the maleic anhydride. This process eliminates clogging problems.

7 Claims, 3 Drawing Figures

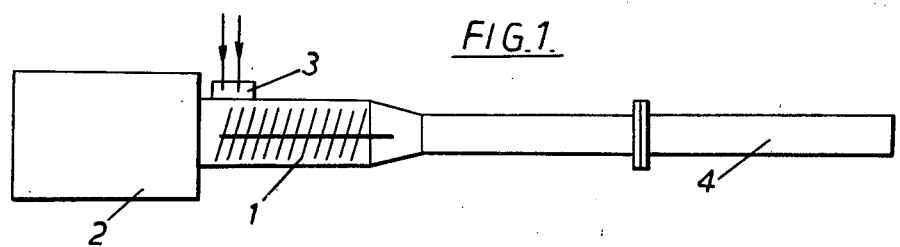
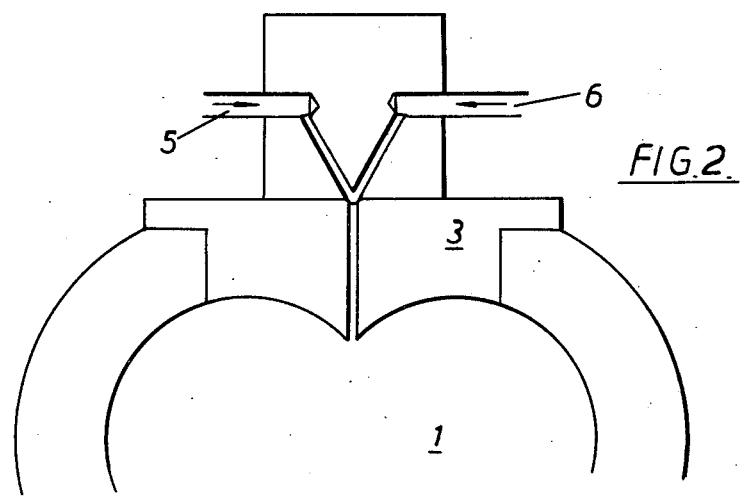
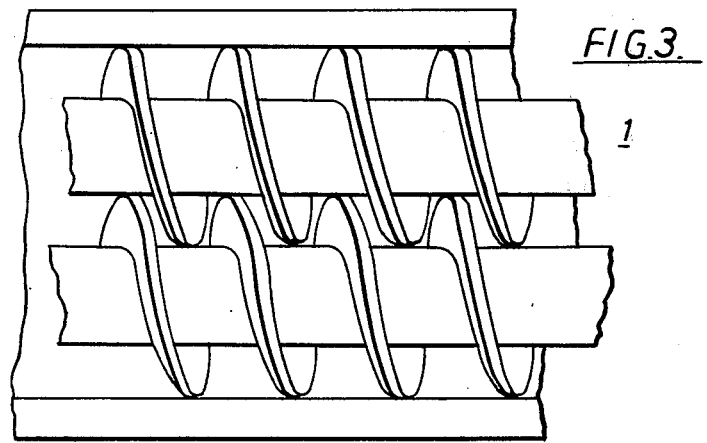

CONTINUOUS PROCESS FOR THE PRODUCTION OF MAEAMIC ACIDS

This is a continuation of application Ser. No. 432,646 filed Jan. 11, 1974, now abandoned.

The present invention relates to a continuous process for the preparation of maleamic acids in suspension.

Various processes which make it possible to produce maleamic acids are known, for example those which are described in U.S. Pats. Nos. 2,444,536 and 2,723,991 and in "Maleic Anhydride Derivatives" by L. A. Flett and W. H. Gardner.

One of these processes consists of reacting maleic anhydride with a primary amine in the presence of an organic diluent which makes it possible to remove the heat produced by the exothermic reaction. A very viscous, thixotropic dispersion which is difficult to pour is thus obtained; the transfer of this dispersion into other vessels in which various conversions or chemical reactions are to be carried out presents great technological difficulties.

A new continuous process for the suspension preparation of maleamic acids has now been found which possesses, especially in the case of bis-maleamic acids, numerous advantages as regards the ease with which it can be carried out, especially because it avoids any risk of clogging.

By maleamic acids, as used herein, are to be understood substances of the formula:

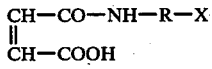

in which R represents a linear or branched alkylene, arylene, aralkylene, alkylarylene or cycloalkylene radical or a divalent heterocyclic radical, the free valencies of which are carried by carbon atoms, the total number of carbon atoms in these various radicals being at most equal to 20 and the minimum number being 2 (in the case of the alkylene radicals), and X represents either a hydrogen atom or the radical

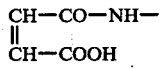

thus giving either mono-or bis-maleamic acids.

According to the present invention there is provided a continuous process for the preparation of a maleamic acid which comprises passing solution of a primary amine (a monoamine or diamine) and a solution of maleic anhydride in an amount such that there is an excess of 5 to 20 mol % relative to the theoretical amount necessary for the reaction with the amine, at a temperature of from 40° to 130° C, and at a rate greater than 7 m/second through an injection nozzle into a twin screw reactor.

The maleic anhydride is suitably dissolved in an anhydrous organic solvent as indicated below, in proportions such that the concentration of the anhydride solution is from 20 to 70% by weight.

Amongst the primary amines which are suitable, there may be mentioned aniline, ethylene-diamine, hexamethylene-diamine, meta-phenylene-diamine, para-phenylenediamine, benzidine, diamino-diphenylmethane, diaminodiphenyl ethers, diamino-diphenyl-sulphones, diaminodicyclohexlylmethanes, diamino-dimethylene-cyclohexanes, diamino-meta-xylylenes, diamino-para-xylylenes, diaminodiphenyl-cyclohexanes, diamino-diphenyl-propanes, diamino-triphenyl-ethanes, diamino-triphenylmethanes and diamino-triazoles.

Amongst the organic solvents which can be used, those with a boiling point between 40° C and 130° C are particularly suitable, especially: hydrocarbons such as benzene, toluene and cyclohexane, chlorinated hydrocarbons such as chlorobenzene and methylene chloride, cyclic and acyclic ethers such as tetrahydrofurane, dioxane and diethyl ether, and dialkyl ketones such as acetone and methyl ethyl ketone.

The solvent for the primary amine can be the same as that used for dissolving the anhydride or can be different provided it is miscible with the first one. Generally the amount of solvent is such that the final concentration of maleamic acid dispersion is from 20 to 70% by weight, preferably from 25 to 60% by weight. The presence of a small amount of water (less than 5% by weight of the amount of solvent) in the amine solution can improve the yields somewhat, but it is not absolutely necessary.

The present invention will now be described, merely by way of example with reference to the accompanying drawings, in which:

FIG. 1 is a schematic view, partly in cross-section of an apparatus suitable for carrying out the process of the present invention;

FIG. 2 is a schematic cross-sectional view showing a typical injection nozzle arrangement; and FIG. 3 is a cross-sectional view of a typical twin-screw reactor.

The apparatus typically comprises a twin screw reactor 1, the dimensions of which are determined by the maleamic acid dispersion flow rate which it is desired to obtain; the ratio of length to the diameter of the screws is preferably from 5/1 to 10/1. The screws are driven in the same direction by a speed-reduction motor 2, advantageously so that they rotate at a rate of from 2 to 30 revolutions/minute.

The reaction of maleic anhydride with the diamine is exothermic; the heat given out can be removed by causing water to flow either through a double jacket attached to the body of the twin screw apparatus or inside the screws themselves or through both. Any other device for removing the heat produced and which can be adapted to the twin screw reactor can also be used.

The solutions of reagents are mixed by passing them through an injection nozzle at a rate greater than 7 m/second. As can be seen from FIG. 2, each solution is introduced via a pipeline 5 and 6, under a pressure which is usually between 1 and 5 bars. The two pipelines join up at the inlet to injection nozzle 3 which can be a cylindrical tube of internal diameter between 0.1 and 2 mm. and of length between 0.5 and 5 cm. The lower end of the nozzle is advantageously bevelled to enable the whole of the aperture to be very close to the screws, preferably within 1 mm. Moreover, this end is situated between the 2 screws and at a tangent to them (not shown). The rotation of the 2 screws carries the maleamic acid dispersion already formed away from the outlet of the injection nozzle and ensures that the end of the latter is permanently clean, preventing it from being clogged. The reaction continues in the dispersion carried away by the double screw.

Optionally, at the end of the twin screw apparatus, it is possible to provide a static mixer which is a cylindrical tube of length between 40 and 80 cm; its diameter depends on the diameter of the screws. The purpose of the static mixer is to increase the time during which the reagents are in contact and thus to achieve higher degrees of conversion.

The following Examples further illustrate the present invention.

EXAMPLE 1

Two solutions are prepared, one containing 1,000 g of maleic anhydride in 2,900 g. of anhydrous acetone, and the other 990 g. of 4,4'-diamino-diphenylmethane in 2,446 g of acetone.

By means of piston pumps, these solutions are continuously conveyed under a pressure of about 4 bars through a nozzle of diameter 0.8 mm and length 24 mm. The rate at which the solutions pass through the nozzle is 9 m/second. The overall flow rate of the reagents is 16.5 l/hour. The injection nozzle opens into a twin screw apparatus, between the 2 screws and at a tangent to the threads of the screw (length of the screws: 32 cm; diameter: 4.5 cm); the apparatus is equipped with a double jacket through which cold water passes, which makes cooling possible. The volume of this apparatus in 380 cm³. The rate at which the screws rotate is approximately 6.8 revolutions/minute and bis-maleamic acid is produced at the rate of 3.5 kg./hour. The dwell time of the reagents in the apparatus is approximately 88 seconds and the degree of conversion, expressed by the ratio of the maleamic acid groups formed to the amine groups employed, is 98%.

A very viscous dispersion of bis-maleimidodiphenyl-methane acid is collected at the outlet of the twin screw apparatus.

EXAMPLE 2

The procedure of Example 1 is followed, with the following changes:

The outlet of the twin screw apparatus is equipped with a static mixer which is a metal tube of diameter 30 mm and length 400 mm. The dwell time of the reagents in the whole of the apparatus is 136 seconds and the degree of conversion is 98.8%.

EXAMPLE 3

Two solutions are prepared, one containing 2,000 g of maleic anhydride in 2,900 g of anhydrous acetone, and the other 1,980 g of 4,4'-diamino-diphenyl-methane in 2,446 g of acetone; in other respects the process was indentical to that in Example 1.

A very viscous dispersion of bis-maleimidodiphenyl-methane acid is obtained with a degree of conversion of 97.5%.

We claim:
1. A continuous process for the preparation of a maleamic acid of the formula:

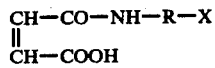

in which R represents the radical

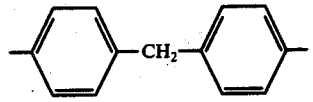

and X represents the radical:

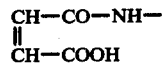

which comprises passing a solution of a primary diamine and a solution of maleic anhydride in amounts such that there is a 5 to 20 mol % excess of anhydride, at a temperature of from 40° to 130° C. and at a rate greater than 7 m/second through an injection nozzle into a twin screw reactor, the solvent for the primary amine being the same as, or miscible with, the solvent for the maleic anhydride.

2. A process according to claim 1 in which the solvent or one of the solvents is a hydrocarbon or chlorinated hydrocarbon, a cyclic or acyclic ether or a dialkyl ketone.

3. A process according to claim 2 in which the solvent for the primary amine and for maleic anhydride is acetone.

4. A process according to claim 1 in which the concentration of the maleic anhydride solution is from 20 to 70% by weight.

5. A process according to claim 1 in which the twin screws have a length/diameter ratio from 5/1 to 10/1.

6. A process according to claim 1 in which the reactor is provided with a water-cooled double jacket.

7. A process according to claim 1 in which the mixture issuing from the reactor is passed to a static mixer.

* * * * *